(12) United States Patent
Sartor et al.

(10) Patent No.: US 7,103,947 B2
(45) Date of Patent: Sep. 12, 2006

(54) MOLDED INSULATING HINGE FOR BIPOLAR INSTRUMENTS

(75) Inventors: Joe Don Sartor, Longmont, CO (US); Dennis J. Harvilla, Lafayette, CO (US)

(73) Assignee: Sherwood Services AG, Schaffhausen (CH)

( * ) Notice: Subject to any disclaimer, the term of this patent is extended or adjusted under 35 U.S.C. 154(b) by 258 days.

(21) Appl. No.: 10/473,618

(22) PCT Filed: Apr. 5, 2002

(86) PCT No.: PCT/US02/11100

§ 371 (c)(1),
(2), (4) Date: Sep. 29, 2003

(87) PCT Pub. No.: WO02/080798

PCT Pub. Date: Oct. 17, 2002

(65) Prior Publication Data
US 2004/0193153 A1 Sep. 30, 2004

Related U.S. Application Data

(60) Provisional application No. 60/281,924, filed on Apr. 6, 2001.

(51) Int. Cl.
*B21K 13/02* (2006.01)
*B21D 53/40* (2006.01)

(52) U.S. Cl. .............................. 29/11; 29/460; 29/527.1

(58) Field of Classification Search ................. 29/11, 29/460, 527.1, 527.2; 606/48, 50, 51
See application file for complete search history.

(56) References Cited

U.S. PATENT DOCUMENTS 2,031,682 A 2/1936 Wapper et al.
3,913,586 A * 10/1975 Baumgarten ............... 606/205

(Continued)

FOREIGN PATENT DOCUMENTS

CA 2104423 2/1994

(Continued)

OTHER PUBLICATIONS

Sigel et al. "The Mechanism of Blood Vessel Closure by High Frequency Electrocoagulation" Surgery Gynecology & Obstetrics, Oct. 1965 pp. 823-831.

(Continued)

*Primary Examiner*—Eric Compton (57) ABSTRACT

An electrosurgical instrument includes a pair of first and second elongated shafts each having an end effector attached to a distal end thereof and a handle. The handle is movable from a first position wherein the end effectors are disposed in spaced relation relative to one another to a second position wherein the end effectors are closer relative to one another. Each of the elongated shafts includes a hinge plate which mounts atop a pivot assembly for effecting movement of the end effectors relative to one another. The instrument also includes a hinge assembly made from an overmold composition which encapsulates and secures the hinge plates and the pivot assembly. The overmold composition is made from an electrically insulating material which insulates the end effectors from one another.

3 Claims, 5 Drawing Sheets

U.S. PATENT DOCUMENTS

| | | |
|---|---|---|
| 4,165,746 A | 8/1979 | Burgin |
| 4,300,564 A | 11/1981 | Furihata |
| 4,370,980 A | 2/1983 | Lottick |
| 4,416,276 A | 11/1983 | Newton et al. |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,715,122 A * | 12/1987 | Linden .................. 30/254 |
| D295,893 S | 5/1988 | Sharkany et al. |
| D295,894 S | 5/1988 | Sharkany et al. |
| 4,763,669 A | 8/1988 | Jaeger |
| 4,827,929 A | 5/1989 | Hodge |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,176,695 A | 1/1993 | Dulebohn |
| 5,190,541 A | 3/1993 | Abele et al. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,244,462 A | 9/1993 | Delahuerga et al. |
| 5,250,047 A | 10/1993 | Rydell |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,318,589 A | 6/1994 | Lichtman |
| 5,324,289 A | 6/1994 | Eggers |
| 5,330,471 A | 7/1994 | Eggers |
| 5,334,183 A | 8/1994 | Wuchinich |
| 5,334,215 A | 8/1994 | Chen |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,423,810 A | 6/1995 | Goble et al. |
| 5,425,739 A | 6/1995 | Jessen |
| 5,429,616 A | 7/1995 | Schaffer |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,140 A * | 10/1995 | Linden et al. ............. 76/106.5 |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A * | 10/1995 | Linden et al. ................ 29/434 |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,558,672 A | 9/1996 | Edwards et al. |
| 5,562,699 A | 10/1996 | Heimberger et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,582,611 A | 12/1996 | Tsuruta et al. |
| 5,585,896 A | 12/1996 | Yamazaki et al. |
| 5,590,570 A | 1/1997 | LeMaire, III et al. |
| 5,591,202 A * | 1/1997 | Slater et al. ................ 606/205 |
| 5,603,711 A | 2/1997 | Parins et al. |
| 5,603,723 A | 2/1997 | Aranyi et al. |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,658,281 A | 8/1997 | Heard |
| 5,662,667 A | 9/1997 | Knodel |
| 5,667,526 A | 9/1997 | Levin |
| 5,674,220 A | 10/1997 | Fox et al. |
| 5,681,282 A | 10/1997 | Eggers et al. |
| 5,693,051 A | 12/1997 | Schulze et al. |
| 5,695,522 A | 12/1997 | LeMaire, III et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,727,428 A | 3/1998 | LeMaire, III et al. |
| 5,735,848 A | 4/1998 | Yates et al. |
| 5,743,906 A | 4/1998 | Parins et al. |
| 5,755,717 A | 5/1998 | Yates et al. |
| 5,766,130 A | 6/1998 | Selmonosky |
| 5,766,166 A | 6/1998 | Hooven |
| 5,766,170 A | 6/1998 | Eggers |
| 5,769,849 A | 6/1998 | Eggers |
| 5,776,128 A | 7/1998 | Eggers |

| | | |
|---|---|---|
| 5,776,130 A | 7/1998 | Buysse et al. |
| 5,779,701 A | 7/1998 | McBrayer et al. |
| 5,792,137 A | 8/1998 | Carr et al. |
| 5,792,177 A | 8/1998 | Kaseda |
| 5,797,938 A | 8/1998 | Paraschac et al. |
| 5,797,958 A | 8/1998 | Yoon |
| 5,800,449 A | 9/1998 | Wales |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,820,630 A | 10/1998 | Lind |
| 5,827,271 A | 10/1998 | Buysse et al. |
| 5,827,279 A | 10/1998 | Hughett et al. |
| 5,827,281 A | 10/1998 | Levin |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,876,401 A | 3/1999 | Schulze et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,902,301 A | 5/1999 | Olig |
| 5,906,630 A | 5/1999 | Anderhub et al. |
| 5,908,420 A | 6/1999 | Parins et al. |
| 5,913,874 A | 6/1999 | Berns et al. |
| 5,921,984 A | 7/1999 | Sutcu et al. |
| 5,935,126 A | 8/1999 | Riza |
| 5,944,718 A | 8/1999 | Austin et al. |
| 5,951,549 A | 9/1999 | Richardson et al. |
| 5,954,720 A | 9/1999 | Wilson et al. |
| 5,976,132 A | 11/1999 | Morris |
| 5,989,277 A | 11/1999 | LeMaire, III et al. |
| 6,004,335 A | 12/1999 | Vaitekunas et al. |
| 6,010,516 A | 1/2000 | Hulka |
| 6,024,741 A | 2/2000 | Willaimson et al. |
| 6,024,744 A | 2/2000 | Kese et al. |
| 6,033,399 A | 3/2000 | Gines |
| 6,039,733 A | 3/2000 | Buysse et al. |
| 6,041,679 A * | 3/2000 | Slater et al. ............... 76/104.1 |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,060,695 A * | 5/2000 | Harle et al. ............... 219/229 |
| 6,083,223 A | 7/2000 | Baker |
| 6,086,586 A | 7/2000 | Hooven |
| 6,090,107 A | 7/2000 | Borgmeier et al. |
| 6,096,031 A | 8/2000 | Mitchell et al. |
| 6,096,037 A | 8/2000 | Mulier et al. |
| 6,099,550 A | 8/2000 | Yoon |
| 6,102,909 A | 8/2000 | Chen et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| H1904 H | 10/2000 | Yates et al. |
| 6,126,658 A | 10/2000 | Baker |
| 6,152,923 A | 11/2000 | Ryan |
| 6,174,309 B1 | 1/2001 | Wrublewski et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,312,430 B1 * | 11/2001 | Wilson et al. ............... 606/50 |
| 6,322,561 B1 | 11/2001 | Eggers et al. |
| 6,334,860 B1 | 1/2002 | Dorn |
| 6,334,861 B1 | 1/2002 | Chandler et al. |
| 6,350,264 B1 | 2/2002 | Hooven |
| 6,352,536 B1 | 3/2002 | Buysse et al. |
| D457,958 S | 5/2002 | Dycus et al. |
| D457,959 S | 5/2002 | Tetzlaff et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,443,970 B1 | 9/2002 | Schulze et al. |
| 6,451,018 B1 | 9/2002 | Lands et al. |
| 6,458,128 B1 | 10/2002 | Schulze |
| 6,458,130 B1 | 10/2002 | Frazier et al. |
| 6,464,704 B1 | 10/2002 | Schmaltz et al. |
| 6,503,248 B1 | 1/2003 | Levine |
| 6,506,189 B1 | 1/2003 | Rittman, III et al. |
| 6,511,480 B1 | 1/2003 | Tetzlaff et al. |
| 6,514,251 B1 | 2/2003 | Ni et al. |
| 6,544,264 B1 | 4/2003 | Levine et al. |
| 6,569,162 B1 | 5/2003 | He |
| 6,585,735 B1 | 7/2003 | Lands et al. |
| 6,620,161 B1 | 9/2003 | Schulze et al. |
| 6,682,528 B1 | 1/2004 | Frazier et al. |
| 6,685,724 B1 | 2/2004 | Haluck |
| 6,733,498 B1 | 5/2004 | Paton et al. |
| 6,743,229 B1 | 6/2004 | Buysse et al. |
| 6,743,230 B1 * | 6/2004 | Lutze et al. ............... 606/51 |
| D496,997 S | 10/2004 | Dycus et al. |
| D499,181 S | 11/2004 | Dycus et al. |
| 6,926,716 B1 | 8/2005 | Baker et al. |
| 6,929,644 B1 | 8/2005 | Truckai et al. |
| 2002/0107517 A1 | 8/2002 | Witt et al. |
| 2002/0188294 A1 | 12/2002 | Couture et al. |
| 2003/0018331 A1 | 1/2003 | Dycus et al. |
| 2003/0069571 A1 | 4/2003 | Treat et al. |
| 2003/0078578 A1 | 4/2003 | Truckai et al. |
| 2003/0139741 A1 | 7/2003 | Goble et al. |
| 2003/0139742 A1 | 7/2003 | Wampler et al. |
| 2003/0158549 A1 | 8/2003 | Swanson |
| 2003/0199869 A1 | 10/2003 | Johnson et al. |
| 2004/0147925 A1 | 7/2004 | Buysse et al. |
| 2004/0225288 A1 | 11/2004 | Buysse et al. |
| 2004/0236325 A1 | 11/2004 | Tetzlaff et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2005/0004568 A1 | 1/2005 | Lawes et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0101951 A1 | 5/2005 | Wham et al. |

| | | |
|---|---|---|
| 2005/0113818 A1 | 5/2005 | Sartor et al. |

FOREIGN PATENT DOCUMENTS

| | | |
|---|---|---|
| DE | 2415263 | 10/1975 |
| DE | 29616210 | 1/1997 |
| DE | 19608716 | 4/1997 |
| DE | 19751108 | 5/1999 |
| DE | 19828976 * | 2/2000 |
| DE | 20001204 * | 3/2000 |
| EP | 0364216 A1 | 4/1990 |
| EP | 0518230 A1 | 12/1992 |
| EP | 0 541 930 B1 | 5/1993 |
| EP | 0572131 | 12/1993 |
| EP | 0572131 A1 | 12/1993 |
| EP | O584787 A1 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | O853922 A1 | 7/1998 |
| EP | 0887046 A3 | 1/1999 |
| EP | 0923907 A1 | 6/1999 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| GB | 2214430 A | 6/1989 |
| JP | 501068 | 9/1984 |
| JP | 502328 | 3/1992 |
| JP | 5-40112 | 2/1993 |
| JP | 06343644 A2 | 12/1994 |
| JP | 07265326 A2 | 10/1995 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 20000342599 A2 | 12/2000 |
| JP | 2001008944 A2 | 1/2001 |
| JP | 2001029356 A2 | 2/2001 |
| JP | 2001128990 A2 | 5/2001 |
| RU | 401367 | 11/1974 |
| SU | 401367 | 11/1974 |
| WO | WO 92/06642 | 4/1992 |
| WO | WO 94/08524 A | 4/1994 |
| WO | WO 95/02369 | 1/1995 |
| WO | WO 95/07662 | 3/1995 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 A | 3/1999 |
| WO | WO 99/40857 | 8/1999 |
| WO | WO 99/51158 | 10/1999 |
| WO | WO 99/66850 A | 12/1999 |
| WO | WO 00/24330 | 5/2000 |
| WO | WO 00/24331 | 5/2000 |
| WO | WO 00/41638 | 7/2000 |
| WO | WO 00/53112 | 9/2000 |
| WO | WO 01/17448 A | 3/2001 |
| WO | WO 01/54604 | 8/2001 |
| WO | WO 01/54604 A1 | 8/2001 |
| WO | WO 02/07627 | 1/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 A1 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | 02/098313 * | 12/2002 |
| WO | WO 04/0432777 | 4/2004 |
| WO | WO 2004/052221 A1 | 6/2004 |
| WO | WO 04/073490 | 9/2004 |
| WO | WO 2004/082495 A1 | 9/2004 |
| WO | WO 2004/098383 A1 | 11/2004 |
| WO | WO 04/103156 | 12/2004 |

OTHER PUBLICATIONS

Bergdahl et al. "Studies on Coagulation and the Development of an Automatic Computerized Bipolar Coagulator" J.Neurosurg, vol. 75, Jul. 1991, pp. 148-151.

Kennedy et al. "High-burst-strength, feedback-controlled bipolar vessel sealing" Surgical Endoscopy (1998) 12: 876-878.

Peterson et al. "Comparison of Healing Process Following Ligation with Sutures and Bipolar Vessel Sealing" Surgical Technology International (2001).

Linehan et al. "A Phase I Study of the LigaSure Vessel Sealing System in Hepatic Surgery" Section of HPB Surger, Washington University School of Medicine, St. Louis MO, Presented at AHPBA, Feb. 2001.

Johnson et al. "Evaluation of the LigaSure Vessel Sealing System in Hemorrhoidectormy" American College of Surgeons (ACS) Clinicla Congress Poster (2000).

Sayfan et al. "Sutureless Closed Hemorrhoidectomy: A New Technique" Annals of Surgery vol. 234 No. 1 Jul. 2001 pp. 21-24.

Heniford et al. "Initial Results with an Electrothermal Bipolar Vessel Sealer" Surgical Endoscopy (2000) 15:799-801.

Heniford et al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics Figo World Congress 2000, Washington, D.C.

Levy et al. "Use of a New Energy-based Vessel Ligation Device During Vaginal Hysterectomy" Int'l Federation of Gynecology and Obstetrics (FIGO) World Congress.

Crawford et al. "Use of the LigaSure Vessel Sealing System in Urologic Cancer Surger" Grand Rounds in Urology 1999 vol. 1 Issue 4 pp. 10-17.

Rothenberg et al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemorrhoidectomy" British Journal of Surgery 2002, 89, 154-157.

Int'l Search Report PCT/US01/11218.

Int'l Search Report PCT/US99/24869.

Int'l Search Report PCT/US98/18640.

Int'l Search Report PCT/US98/23950.

PCT/US01/11340, International Search Report.

PCT/US01/11420, International Search Report.

PCT/US02/01890, International Search Report.

PCT/US02/11100, International Search Report.
PCT/US04/03436, International Search Report.
PCT/US04/13273, International Search Report.
PCT/US04/15311, International Search Report.
EP 98944778, International Search Report.
EP 98958575, International Search Report.
EP 04027479, International Search Report.
EP 04027705, International Search Report.
EP 04027314, International Search Report.
"Innovations in Electrosurgery" Sales/Product Literature.
LigaSure Vessel Sealing System, the Seal of Confidence in General, Gynecologic, Urologic, and Laparaoscopic Surgery Sales/Product Literature.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC.
"Reducing Needlestick Injuries in the Operating Room" Sales/Product Literature.
Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery" Sales/Product Literature.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With The LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.

McLellan et al. "Vessel Sealing For Hemostasis During Gynecologic Surgery" Sales Product Literature.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3.
E. David Crawford "Use of a Novel Vessel Sealing Technology in Management of the Dorsal Veinous Complex" Sales Product Literature.
Jarrett et al., "Use of the LigaSure Vessel Sealing System for Perl-Hilar Vessels in Laparoscopic Nephrectomy" Sales Product Literature.
E. David Crawford "Evaluation of a New Vessel Sealing Device in Urologic Cancer Surgery" Sales Product Literature.
Joseph Ortenberg "LigaSure System Used in Laparoscopic 1st and 2nd Stage Orchiopaxy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
Dulemba et al., "Use of a Bipolar Electrothermal Vessel Sealer in Laparoscopically Assisted Vaginal Hysterectomy" Sales Product Literature.
Johnson et al., "Evaluation of a Bipolar electrothermal Vessel Sealing Device in Hemorrhoidectomy" Sales Product Literature.
"Innovations in Electrosurgery" Sales/Product Literature: Dec. 31, 2000.
LigaSure Vessel Sealing System, the Seal of Confidence in General, Gynecologic, Urologic, and Laparaoscopic Surgery Sales/Product Literature: Jan. 2004.
Olsson et al. "Radical Cystectomy in Females" Current Surgical Techniques in Urology, vol. 14, Issue 3, 2001.
Dulemba et al. "Use of a Bipolar Electrothermal Vessel Sealer in Laparoscopically Assisted Vaginal Hysterectomy" Sales Product Literature: Jan. 2004.
Johnson et al. "Evaluation of a Bipolar electrothermal Vessel Sealing Device in Hemorhoidectomy" Sales Product Literature: Jan. 2004.
International Search Report PCT/US01/11224 dated Nov. 13, 2001.
International Search Report EP 98958575.7 dated Sep. 20, 2002.
International Search Report EP 04013772 dated Apr. 1, 2005.
International Search Report EP 05013895 dated Oct. 14, 2005.
International Search Report EP 05017281 dated Nov. 16, 2005.
US 6,090,109, 07/2000, Lands et al. (withdrawn)
US 6,663,629, 12/2003, Buysse et al. (withdrawn)

* cited by examiner

MOLDED INSULATING HINGE FOR BIPOLAR INSTRUMENTS

CROSS REFERENCE TO RELATED APPLICATION

This application claims the benefits of and priority to U.S. Provisional Patent Application Ser. No. 60/281,924 entitled: "MOLDED INSULATING HINGE FOR BIPOLAR INSTRUMENT" which was filed on Apr. 6, 2001 by Sartor et al., the entire contents of this application are hereby incorporated by reference herein.

BACKGROUND

1. Technical Field

The present disclosure relates to joints and hinges which connect movable components of an electrosurgical instrument and methods for fabricating hinges for movable components of an electrosurgical instrument. More particularly, the present disclosure relates to an easily customizable hinge made from a plastic overmold composition which connects two end effectors for relative movement therebetween. The present disclosure also relates to a method for fabricating the overmolded hinge.

2. Background of Related Art

Typically, joints and hinges for electrosurgical instruments which connect movable components are formed from an insulating material to prevent shorting between component parts and/or prevent the formation of alternate current paths through the instrument. As such, instrument designers have manufactured electrosurgical instruments which involve complex rotating hinge configurations to isolate, insulate and/or control the electrosurgically active areas of the instrument. For example, traditional metal hinge configurations typically include multiple independent subassemblies which are overmolded with plastic material having high bond strengths. These separately overmolded subassemblies are mechanically integrated and arranged in a series of manufacturing steps that often require tightly controlled and time consuming processes to achieve proper jaw alignment and reliable and consistent gap separation between electrodes. Moreover, additional steps are often undertaken to control other parameters associated with the rotational movement about the hinge, e.g., friction, torque, etc.

Thus, a continuing need exists for a simple and effective insulating hinge that can be readily integrated into the manufacturing process to electrically isolate the movable components of an electrosurgical instrument. Further need exists for the development of a simplified manufacturing process which effectively fabricates an electrosurgical instrument which includes an insulated hinge that isolates and integrates the electrically active components of the instrument and results in the repeated formation of a reliable and easily customizable instrument which meets specific tolerance requirements for proper jaw alignment and gap distances.

SUMMARY

An electrosurgical instrument includes a pair of first and second elongated shafts each having an end effector attached to a distal end thereof and a handle. The handle is movable from a first position wherein the end effectors are disposed in spaced relation relative to one another to a second position wherein the end effectors are closer relative to one another. Each of the elongated shafts includes a hinge plate which mounts atop a pivot assembly for effecting movement of the end effectors relative to one another. The instrument also includes a hinge assembly which is overmolded to encapsulate and secure the hinge plates and the pivot assembly. The hinge assembly is made from an electrically insulating material which insulates the end effectors from one another.

Preferably, the hinge assembly is made from a composition of materials selected from the group consisting of: polyamides, nylon, arcylanitride-butane nitro styrene acetyl, polyesters, syndiotactic-polystryrene (SPS), polybutylene terephthalate (PBT), polycarbonate (PC), acrylonitrile butadiene styrene (ABS), polyphthalamide (PPA), polymide, polyethylene perephthalate (PET), polyamide-imide (PAI), acrylic (PMMA), polystyrene (PS and HIPS), polyether sulfone (PES), aliphatic polyketone, acetal (POM) copolymer, polyurethane (PU and TPU), nylon with polyphenylene-oxide dispersion and acrylonitrile styrene acrylate. In another embodiment, the hinge assembly is made from a composition of lubricating materials selected from the group consisting of: silicon, molybdenum disulfide and light olefins.

In one embodiment, the pivot assembly includes a pivot pin integrally associated with a first of the hinge plates and a pivot hole formed within a second of the hinge plates. Preferably, the pivot pin is made from an electrically insulating material. In another embodiment, the overmold composition of the hinge assembly is disposed between the pivot pin and the pivot hole to electrically insulate each of the hinge plates from one another.

In yet another embodiment, the hinge assembly includes a retention tab which secures the hinge assembly between the hinge plates. Preferably, the retention tab is formed during the overmold process as the overmold composition leaches through the pivot pin to form a tab on the outer-facing surface of the hinge plate. Once the retention tab cures, the hinge assembly is securely held between the hinge plates. In still yet another embodiment, the hinge assembly includes a stop member for limiting the movement of the end effectors relative to one another.

The present disclosure also relates to a method of forming a hinge assembly and includes the steps of: providing a pair of first and second elongated shafts each having an end effector attached to a distal end thereof, a handle and a hinge plate. The handle is dimensioned to effect movement of the end effectors relative to one another. The method further includes the step of mounting the elongated shafts to a die block, introducing an overmold composition into the die block to encapsulate at least a portion of the hinge plates and curing the overmold composition to form the hinge assembly.

In another embodiment, the method further includes the step of: selectively positioning at least one spacer between the end effectors to maintain a gap distance between the end effectors during the molding and curing step.

BRIEF DESCRIPTION OF THE DRAWINGS

Preferred embodiments of the presently disclosed surgical instrument having a molded insulating hinge assembly are described herein with reference to the drawings, wherein.

DETAILED DESCRIPTION

Referring now in specific detail to the drawings in which like reference numerals identify similar or identical elements throughout the several views, and initially to FIGS. 1–3C, one particular embodiment of an electrosurgical instrument 10 includes two elongated shafts 30 and 60 each having a distal end effector 32, 62 and a proximal handle portion 34 and 64, respectively. Handles 34 and 64 are movable relative to one another about a hinge assembly 20 from a first position wherein the distal end effectors 32, 62 are positioned in spaced relation relative to one another to a second position in which the distal end effectors 32, 62 cooperate to grasp tissue therebetween. It is envisioned that handles 34 and 64 may take any design configuration suitable for manipulation or control of the surgical instrument 10.

Each distal end, e.g., 32, has a jaw member 36 disposed at the distal end thereof which includes a tissue grasping surface 38 dimensioned to cooperate with the other jaw member, e.g., 66, and other tissue grasping surface, e.g., 68, to grasp tissue and other luminal structures upon actuation of the handles 34 and 64. The jaw members 36, 66 each also include a hinge plate 35, 65, respectively, which cooperate to support opposing sides of the hinge assembly 20 as explained in more detail below. Hinge plate 35 includes a pivot pin 74 which mechanically engages a corresponding pivot hole 61 disposed within hinge plate 65 to form pivot assembly 70.

Hinge assembly 20 as described herein relates to one particular embodiment for use with a bipolar electrosurgical forceps 10, however, it is contemplated that the presently disclosed hinge assembly 20 could be dimensioned for use with other electrosurgical instruments including vessel sealing instruments, grasping instruments, ablation instruments, electrosurgical scissors, etc. Moreover, it is also envisioned that the hinge assembly 20 may be configured for use with a broad range of other non-electrical surgical instruments such as pliers, scissors, shears, crimpers and wire cutters.

Figure 1:
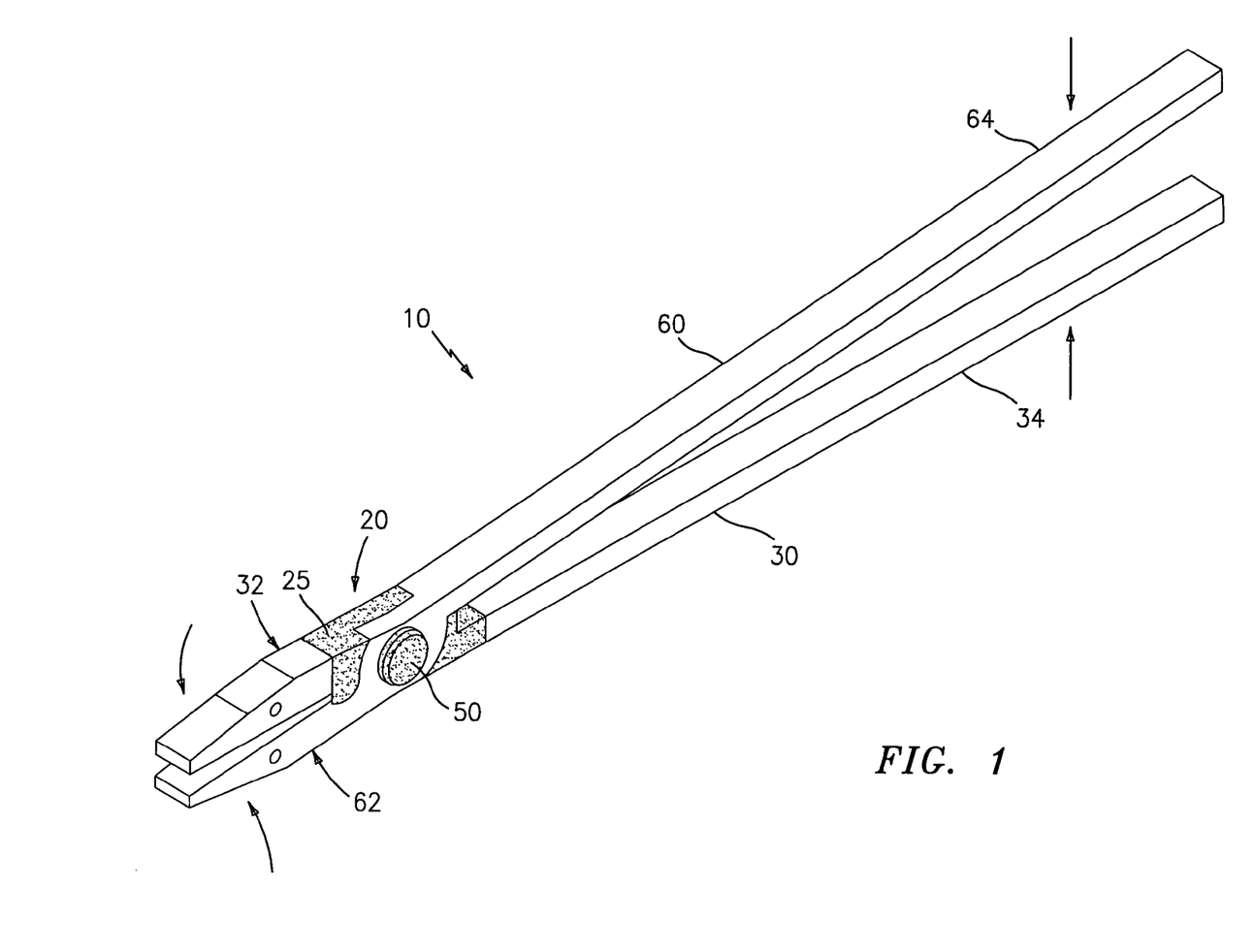
FIG. 1 is a perspective view of one embodiment of a bipolar forceps having a molded insulating hinge assembly constructed in accordance with the present disclosure.
Figure 2A:
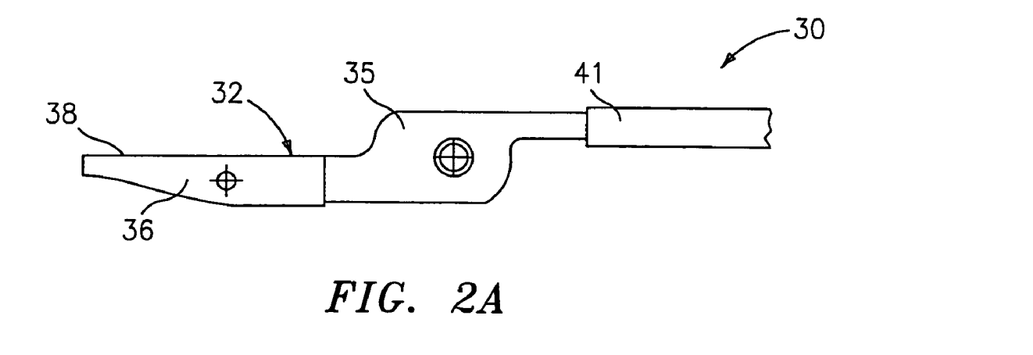
FIG. 2A is an enlarged, right, side view of an end effector of the bipolar forceps of FIG. 1 prior to overmolding.
Figure 2B:
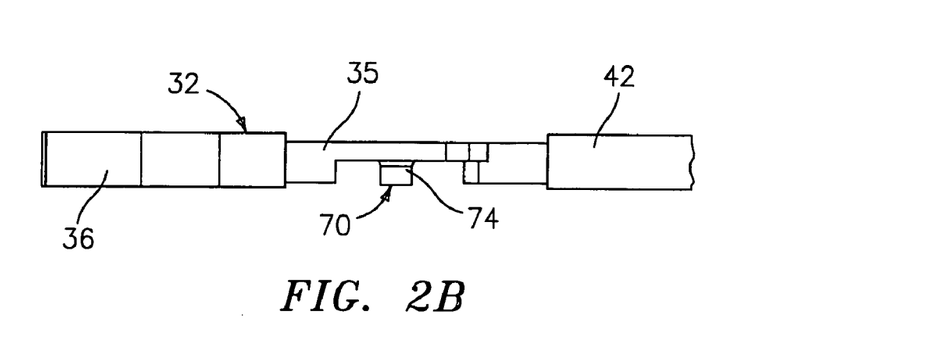
FIG. 2B is a bottom view of the end effector of FIG. 2A.
Figure 2C:
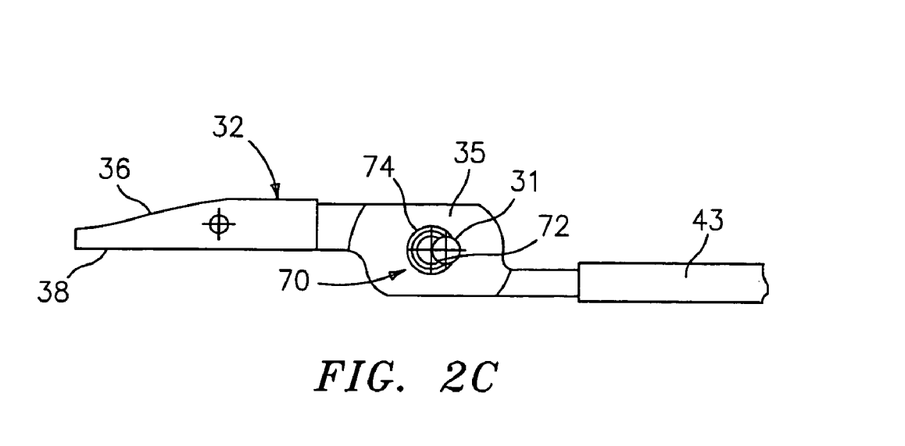
FIG. 2C is a left, side view of the end effector of FIG. 2A.
Figure 3A:
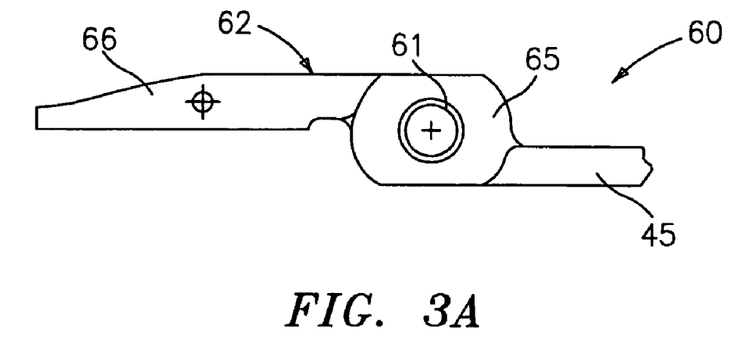
FIG. 3A is an enlarged, right, side view of a second end effector of the bipolar forceps of FIG. 1 prior to overmolding.
Figure 3B:
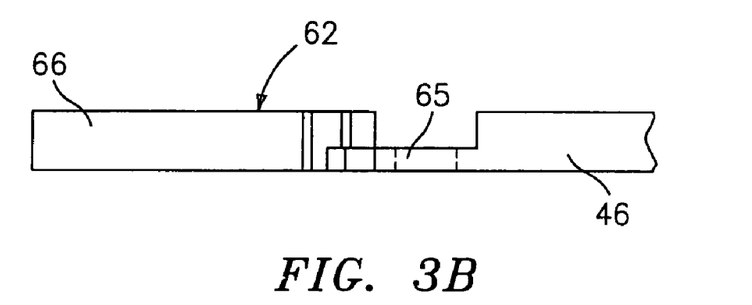
FIG. 3B is a bottom view of the end effector of FIG. 3A.
Figure 3C:
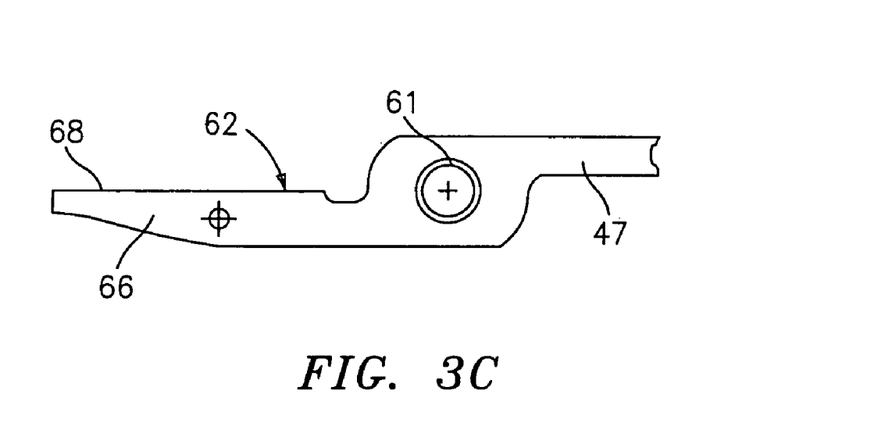
FIG. 3C is a left, side view of the end effector of FIG. 3A.

Preferably, hinge assembly 20 is made from a composition 25 of insulating material such as plastic which is overmolded to encapsulate the hinge plates 35, 65 during the manufacturing process. As best seen in FIG. 2C, pivot pin 74 includes a reinforcing portion 72 which allows the mold composition 25 to extrude through the pivot pin 74 of hinge plate 35 to an opposite side 63 of hinge plate 65 to form a retention tab 50. More particularly, after a significant amount of mold composition 25 is extruded around the reinforcing portion 72 of the pivot pin 74, the retention tab 50 is stamped against the opposite side 63 of hinge plate 65 to secure the hinge plates 35 and 65 in close abutment about the pivot assembly 70. As can be appreciated in this embodiment of the present disclosure, the mold composition 25 is contiguous with the exterior of the hinge plate 35 through aperture 31, around reinforcing portion 72 and with the retention tab 50 which securely engages the hinge assembly 20 between the hinge plates 35, 65.

As can be appreciated, both the mold composition 25 and the retention tab 50 are formed during the same molding step resulting in the formation of the hinge assembly 20. It is envisioned that once cured, the retention mechanism 50 forms a structural limit that at least partially controls the alignment of the distal end effectors 32 and 62 as well as the amount of pivotal movement between the jaw members 36 and 66. Alternatively, the retention tab 50 may be made from the same or a different mold composition 25 and is designed to mechanically engage the pivot pin 74 or the hinge plate 65 to secure the hinge assembly between the hinge plates 35 and 65.

Figure 4:
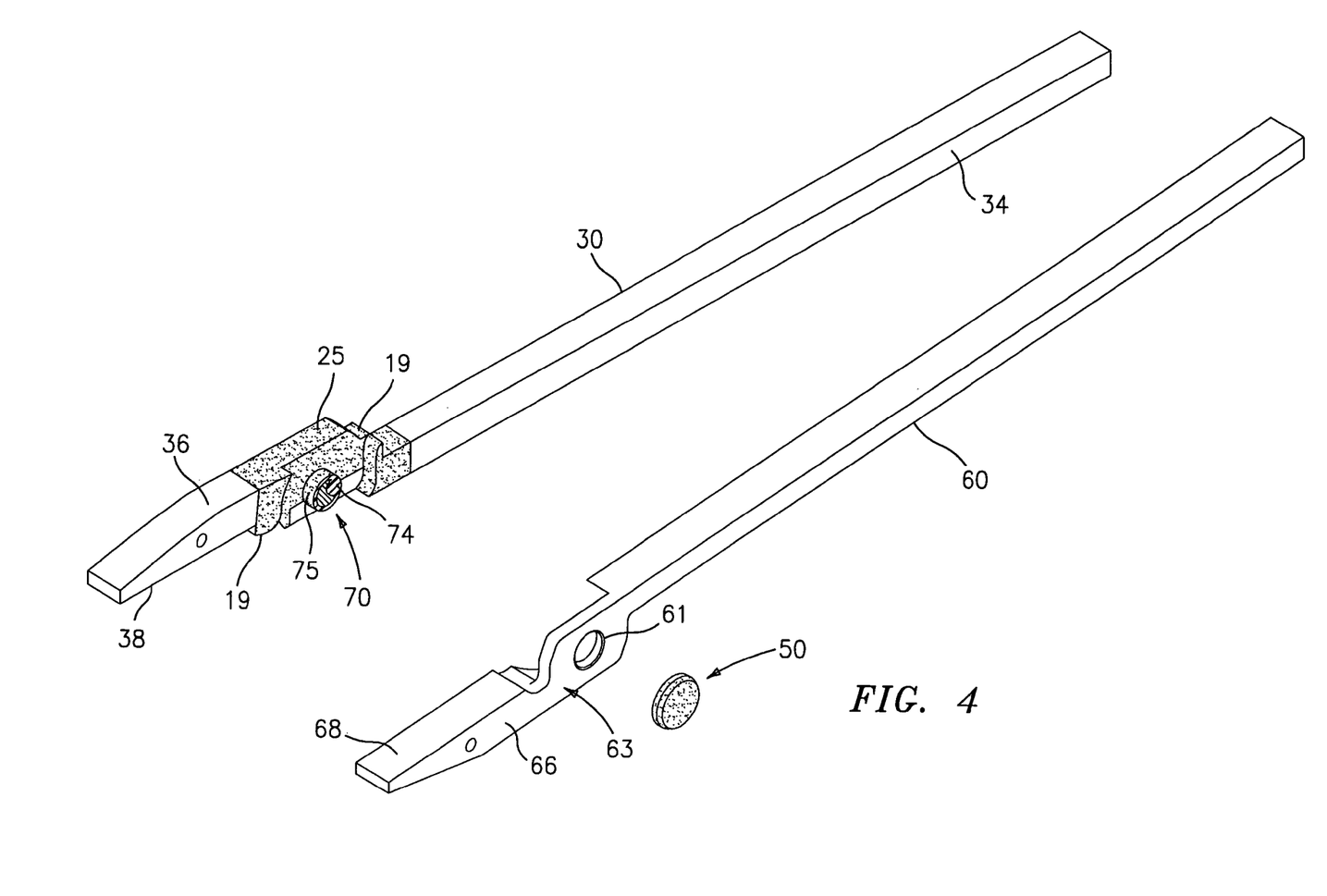
FIG. 4 is an exploded, perspective view of the bipolar instrument of FIG. 1.

As best shown in the exploded view of FIG. 4, the formation of the hinge assembly 20 in this manner electrically isolates the two end effectors 32 and 62 and the component parts thereof enabling a user to selectively apply electrosurgical energy through the tissue and between the jaw members 36 and 66 as needed. More particularly, during the overmold process, the plastic cures about the outer periphery 75 of pivot pin 74 which electrically isolates hinge plate 35 from hinge plate 65. As can be appreciated, the retention tab 50 which, as mentioned above, is also formed of plastic which extrudes through pivot pin 74 to the opposite side 63 of hinge plate 65, not only retains the two hinge plates 35 and 65 in secure abutment about the pivot assembly 70 but also electrically isolates the hinge plates 35 and 65 from one another.

Because the presently disclosed hinge assembly 20 is preferably formed during a single manufacturing step, it can be easily customized and dimensioned to suit a particular purpose or to achieve a particular result. For example, the alignment of the jaw members 36 and 66, e.g., jaw angle or jaw offset, may be easily customized depending upon a particular purpose. Moreover, the formation of a gap distance between the jaw members 36, 66 may be easily customized. For example, the hinge assembly 20 may be molded or formed during the manufacturing process such that the jaw members 36 and 66 maintain a consistent and specific gap distance within the range of about 0.001 inches to about 0.005 inches at closure. The formation of the gap distance is discussed below with particular reference to FIG. 5.

Generally, hinge 20 is formed from an overmold composition containing a joint-forming base resin material and a lubricating component. Hinge-forming materials for use herein can be any commercially available materials known to one skilled in the art for toughness and strength as well as being capable of injection molding. Suitable joint-forming base resin materials include, but are not limited to, polyamides such as nylon, arcylanitride-butane nitro styrene; acetyl, polyesters, etc. Preferably, the overmold composition is made from a plastic or plastic-based material having a Comparative Tracking Index of about 300 volts to about 600 volts for dielectric isolation. For example, the overmold composition 25 may be made from a group of materials selected from a group which includes Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate. Alternatively, it is envisioned that a non-plastic insulating material, e.g., ceramic, may be used in lieu of or in combination with one or more of the above-identified materials to facilitate the manufacturing process and possibly contribute to more uniform and consistent transfer of electrosurgical energy across the tissue.

Suitable lubricating components for use with the base resin material include a broad range of materials known to compliment the overmold composition to provide mold having a low bonding strength with good surface lubricating qualities. Such lubricating components include, but are not limited to, silicon-like materials, molybdenum disulfide, light olefins, etc. Depending upon the overall composition of the base resin material being used, a lubricating component may not be required.

It is also anticipated that additional materials may be employed in combination with the above materials to achieve suitable levels of toughness and strength in the molded hinge 20. These additional materials may include, for example, reinforcing agents such as glass fibers, ground glass, or elongated glass fibers. For example, in one particular embodiment, hinge assembly 20 is formed from a commercially available nylon material having about 2.5 wt. % glass fiber reinforcing material and a silicone lubricating component in the range of about 0.75 wt. % to about 10 wt. %. In another embodiment, hinge assembly 20 may be formed from a nylon having glass fiber reinforcing material in the range of about 5 wt. % to about 40 wt. % and silicone in the range of about 2 wt. % to about 8 wt. %.

While silicone or other lubricating agents are typically used in injection molding processes, it has been found that the amount of silicone should be tightly controlled to provide uniform and consistent curing and operating efficiencies. It is envisioned that the silicone component of the overmold composition creates a sustained lubricated surface at the interface between hinge plates 35 and 65. It has also been found that increasing the level of silicone, e.g., amounts greater than 2 wt. %., in the joint-forming material of hinge assembly 20, produces an overmold composition having a low bond strength. As can be appreciate, although the overmold composition 25 has a low bond strength to the surrounding metals, i.e., elongated shafts 30, 60 and hinge plates 35, 65, the low bonding strength is offset by a the mechanical advantages of the retention tab 50 and aperture 31.

As mentioned above, the presently disclosed hinge assembly 20 may be formed during a single manufacturing step and may be easily customized depending upon a particular purpose or to achieve a particular result. For example, parameters such as self lubrication of the hinge assembly 20, hinge assembly 20 strength, jaw member 36, 66 alignment, e.g., jaw angle or jaw offset, isolation of the jaw members 36 and 66 during electrosurgical application and the formation of a gap distance between the jaw members 36 ad 66 (or electrodes or probes attached to the jaw members 36 and 66) may be easily achieved.

The present application is not limited to the above identified materials, but contemplates a broad range of overmold composition 25 in varying combinations and amounts that provide an overmold composition suitable for the function of hinge assembly 20. It is envisioned that applications described herein relating to the injection overmolding of thermoplastic polyamides, for example, may be translated into other areas including, but not limited to, other engineering plastic materials, engineering metals and ceramics that may be selectively applied in varying insulative as well as mechanical applications.

The overmold composition 25 of the present disclosure is configured to create a tough and strong hinge assembly 20 by at least partially encapsulating the hinge plates 35 and 65 and the pivot assembly 70 (and the various components thereof). The overmold composition 25 provides suitable strength as a result of its continuity of encapsulation as well as the ability of the overmold composition 25 to form surface features which are specifically dimensioned to improve the strength of the hinge assembly 20 once cured. For example, features within the pivot pin 74 and features within the pivot hole 61 may be provided to increase the overall strength of the instrument and/or hinge assembly 20, e.g. notches, detents, cavities, overmolded posts, etc. Further, structural strength for the hinge assembly 20 may be gained by coating or filling features defined in the surface of the hinge plates 35, 65 to augment the mechanical bonding of the plastic mold with the hinge plates 35, 65, pivot pins 74 and pivot holes 61. For example, surface undulations such as lip structures, overhanging shapes, concave shapes, or cantilevered structures having different geometric shapes may be employed to mechanically engages the hinge assembly 20 to the hinge plates 35.

Preferably, the elongated shafts 30, 60 are made from a stainless steel material. However, other metal alloys, plastics, ceramics, or composites are also contemplated including combinations of one or more plastics, composites, metals, graphite, carbon-coated plastics and/or any other conductive materials which are well suited for overmolding purposes. Preferably, the elongated shafts 30 and 60 are die-cut, stamped, or micro-machined such that the end effectors 32 and 62 and the hinge plates 35 and 65 from integral parts thereof. As can be appreciated, making these elements integral and utilizing the overmold hinge assembly 20 as presently disclosed herein greatly simplifies the overall manufacturing and assembly processes.

Instrument 10 may also include surface treatments (e.g., nylon powder coatings, chemical treatments, nickel alloy coatings, mechanical finish treatments, shrink tubing, etc.) which facilitate manipulation of the tissue structures, enhance conduction of electrosurgical energy across the jaw members 36, 66 and/or reduce the likelihood of inconsistencies across the treatment area which may lead to collateral tissue damage, flashover, thermal spread, arcing, etc.

Preferably, the thickness of the hinge assembly 20 can be selectively altered depending upon a particular purpose or for use with a certain instrument. The ultimate thickness and strength of the overmold composition 25 is also related to the viscosity of the overmold composition 25 and the duration and temperature of the curing process. For example, the hinge assembly 20 may include a range of thickness from about 0.020 to about 0.040 inches in thickness. The thickness of the overmold composition 25 also depends on mechanical load bearing and dimensional requirements of a particular application.

As best shown in FIG. 4, the outer periphery 75 of pivot pin 74 provides a basis for the formation of additional molded material around the pivot pin 74 which not only electrically insulates the jaw members 36 and 66 from one another but also reduces the chances of the pivot slipping or rotating when torquing, cross-loading, or shearing forces are applied during the normal use of instrument 10.

It is envisioned that the hinge assembly may be designed as a more complex mechanism and/or may be designed to encapsulate a more complex pivoting mechanism. For example, it is contemplated that the hinge assembly 20 may include various multiple-link systems such as a two-bar, three-bar or four-bar linkage or may include a two-step hinge. The pivot pin 74 and/or the pivot hole 61 may also be dimensioned in a variety of different shapes and sizes depending upon a particular purpose or to achieve a particular result, e.g., cam and cam-follower, arcuate, elliptical, etc. It is also envisioned that the hinge assembly 20 may include one or more stop members 19 which limit the overall distance that the jaw members 36, 66 may pivot in either the open or closed positions. The stops 19 may be configured in steps or as a cantilevered feature to define more than one gap distance between jaw members 36 and 66.

In one embodiment, retention tab 50 may be configured to mechanically engage a portion of the hinge plate 65 and/or pivot pin 74 which is contemplated to serve two purposes: 1) to mechanically retain the retention tab 50 against the hinge plate 65 and further secure the instrument 10 as assembled; and 2) to bias the pivot assembly 70 to a predetermined open, closed, or intermediary position. For example, the outer-facing surface 63 of hinge plate 65 may be provided with slots or grooves (not shown) which mechanically engage the retention tab 50.

With respect the to particular surgical instrument of FIGS. 1–4, i.e., bipolar forceps 10, first and second conductive wires 41 and 45 are each electrically coupled to a respective distal end effector 32 and 62 at one end thereof and ultimately connected to an electrosurgical generator (not shown) at the opposite end thereof. The first electrical conductor 41 (see FIG. 2A) connects the first jaw member 36 to a first electrical potential and the second electrical conductor 45 (see FIG. 3A) connects the second jaw member 66 to a second electrical potential. Preferably, the first and second electrical conductors 41 and 45 are disposed within longitudinally-oriented channels defined within elongated shafts 30 and 60, respectively. The channels are preferably oriented and dimensioned to facilitate mechanical engagement of the electrical conductors 41 and 45 with the respective jaw members 36 and 66 in such a manner to allow free, pivotable movement of the jaw members 36 and 66 relative to one another. Preferably, the cable leads are attached to the electrically conductive jaw members 36 and 66 by a crimp-like electrical connection (not shown). As mentioned above, the hinge assembly 20 includes at least one stop 19 which abuts against elongated shafts 30, 60 to prevent over-rotation of the jaw members 36 and 66 to avoid straining the electrical leads.

Preferably, hinge assembly 20 is manufactured in a single injection molding or manufacturing process step in which elongated shafts 30 and 60 are mounted atop a die block within an injection molding machine. The overmold composition 25 of the hinge assembly 20 is then injected between the jaw members 36 and 66 to encapsulate the hinge plates 35 and 65 and the pivot assembly 70. As mentioned above, the hinge assembly 20 is strengthened by the continuity of the plastic overmold composition 25 which extrudes through the pivot pin 74 and pivot hole 61 to form the retention tab 50. Thus, in one particular embodiment, the hinge assembly 20 is completely formed by overmold composition flowing around and through the various components parts of the hinge assembly 20 and the pivot assembly 70. As mentioned above, the retention tab may be a separate component made from the same or a similar composition which is dimensioned to mechanically engage the pivot pin 74 or the outer-facing surface 63 of the hinge plate 65.

Figure 5:
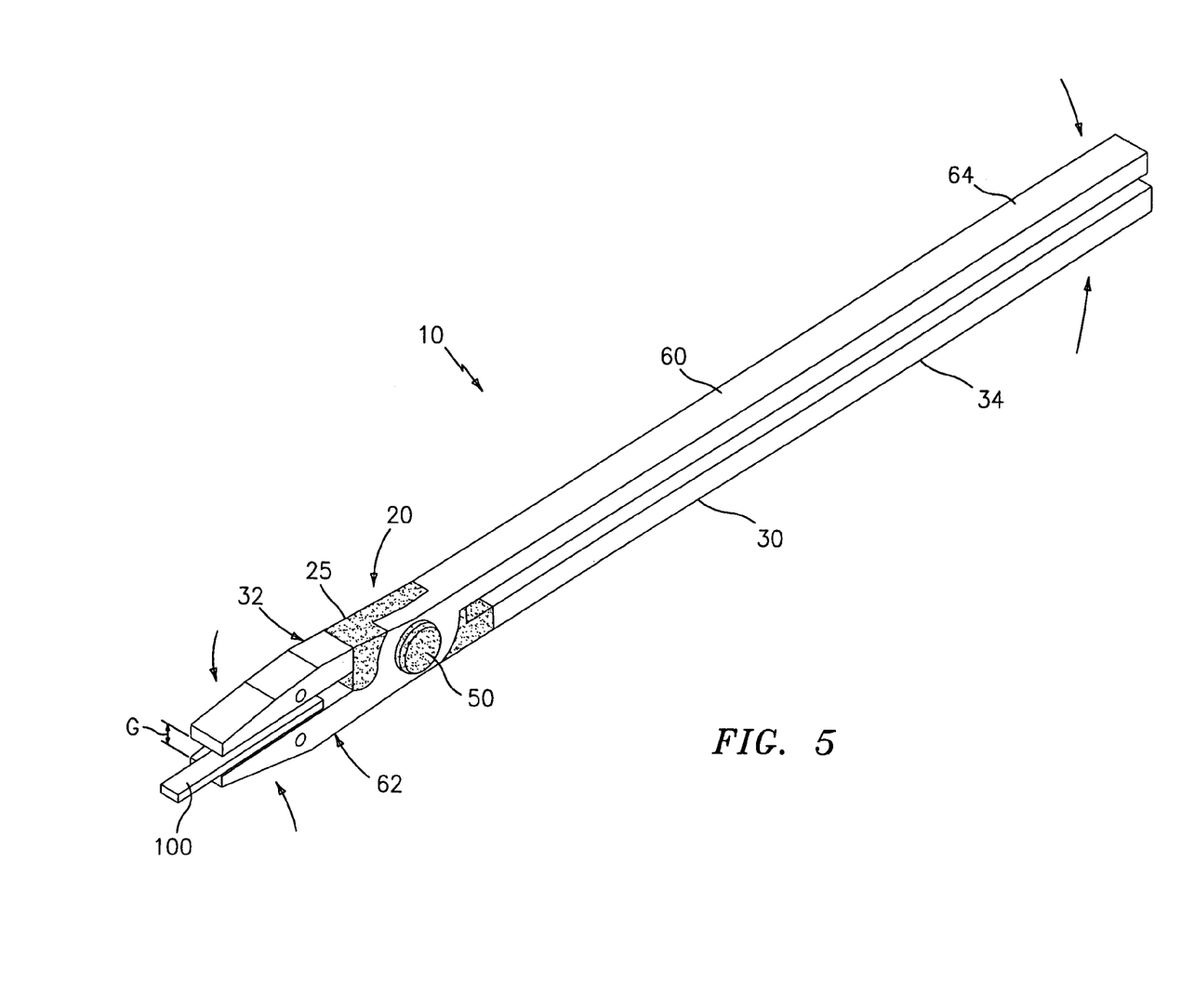
FIG. 5 is a perspective view of the embodiment shown in FIG. 1 shown with a spacer disposed between a pair of jaw members to fix a specific gap distance during the overmolding process.

As mentioned briefly above and as shown in FIG. 5, a spacer 100 may be positioned between jaw members 36 and 66 prior to the overmolding process. The spacer 100 sets a fixed gap distance "G" between jaw members 36 and 66 at closure (i.e., when the jaw members 36 and 66 are disposed in the closed or tissue grasping position) by limiting the formation of the stop 19 during the overmolding process. As can be appreciated, different and/or customized gap distances "G" between the jaw members 36 and 66 can be easily formed depending upon a particular purpose or to achieve a particular result.

The presently disclosed overmolding process also enables the manufacturer to customize the precise alignment of the jaw members 36 and 66 relative to one another. Thus, in applications in which the alignment of jaw members 36 and 66 is critical, such as for shearing, cutting and sealing, the accuracy, alignment and configuration of the hinge assembly 20, pivot assembly 70 and jaw members 36 and 66 can be easily customized. Further, the presently disclosed process also provides a repeatable and reliable alignment tool for mass manufacturing of surgical instruments according to specific tolerances.

From the foregoing and with reference to the various figure drawings, those skilled in the art will appreciate that certain modifications can also be made to the present disclosure without departing from the scope of the present disclosure. For example, it is contemplated that hinge assembly 20 can be configured to join a plurality of different components or subassemblies in the assembly depending upon a particular purpose. Moreover, the outer periphery 75 of pivot pin 74 could also include features such as a series of undulations or knurling, or a series of radially aligned cavities having features within those cavities that strengthen the mechanical interface of the overmold composition to the pivoting assembly 70.

In one embodiment, the instrument includes a conductive strip (not shown) disposed through one shaft, e.g., shaft 30. Electrosurgical wires or cables (not shown) from an electrosurgical generator (not shown) connect the two electrical potentials to the conductive strip. The opposite end of the conductive strip includes one electrical connection to end effector 32 and a second electrical connection to pivot assembly 70 which provides electrical continuity to the opposite end effector 62. More particularly, the second electrical connection of the conductive strip makes contact across the moving junction of the pivot assembly. It is not necessary that the conductive strip wrap around the pivot pin 74 between the instrument halves because during the molding process the conductive strip is forced into intimate contact with the opposite end effector 62, i.e, the flow of the uncured hinge material positions the conductive strip into contact with end effector 62.

As a result thereof, secondary washers or force loading devices are not required to initiate contact between the conductive strip and the opposite end effector 62. The conductive strip my also include a series of wave-like folds, e.g., accordion folds, which give the conductive strip a spring-like quality and which fosters contact with the opposite end effector 62 during and after curing. As can be appreciated, this arrangement assures that a moving or sliding contact is maintained between the conductive strip and the end effector 62 during movement, i.e., pivoting, of the end effectors relative to one another.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. A method of forming a hinge assembly comprising the steps of:
   providing a pair of first and second elongated shafts each having an end effector attached to a distal end thereof, a handle and a hinge plate, said handle effecting movement of the end effectors relative to one another;
   mounting said elongated shafts to a die block;
   introducing an overmold composition into said die block to encapsulate at least a portion of said hinge plates;
   selectively positioning at least one spacer between said end effectors to maintain a gap distance between said end effectors during the curing step; and
   curing said overmold composition to form said hinge assembly.

2. A method according to claim 1 wherein said overmold composition of said introducing step includes materials selected from the group consisting of polyamides, nylon, arcylanitride-butane nitro styrene acetyl, polyesters, syndiotactic-polystryrene (SPS), polybutylene terephthalate (PBT), polycarbonate (PC), acrylonitrile butadiene styrene (ABS), polyphthalamide (PPA), polymide, polyethylene perephthalate (PET), polyamide-imide (PAI), acrylic (PMMA), polystyrene (PS and HIPS), polyether sulfone (PES), aliphatic polyketone, acetal (POM) copolymer, polyurethane (PU and TPU), nylon with polyphenylene-oxide dispersion and acrylonitrile styrene acrylate.

3. A method according to claim 1 wherein said overmold composition of said introducing step includes lubricating materials selected from the group consisting of silicon, molybdenum disulfide and light olefins.

* * * * *